(12) United States Patent
Limaye (10) Patent No.: US 11,717,604 B2
(45) Date of Patent: Aug. 8, 2023

(54) PEN NEEDLE STORAGE (71) Applicant: Embecta Corp., Andover, MA (US)

(72) Inventor: Amit Limaye, Wayne, NJ (US)

(73) Assignee: Embecta Corp., Andover, MA (US)

(*) Notice: Subject to any disclaimer, the term of this patent is extended or adjusted under 35 U.S.C. 154(b) by 0 days.

(21) Appl. No.: 17/049,779

(22) PCT Filed: Apr. 26, 2019

(86) PCT No.: PCT/US2019/029281
§ 371 (c)(1),
(2) Date: Oct. 22, 2020

(87) PCT Pub. No.: WO2019/210126
PCT Pub. Date: Oct. 31, 2019

(65) Prior Publication Data
US 2021/0236714 A1     Aug. 5, 2021

Related U.S. Application Data

(60) Provisional application No. 62/663,597, filed on Apr. 27, 2018.

(51) Int. Cl.
*A61M 5/00* (2006.01)
*A61M 5/32* (2006.01)

(52) U.S. Cl.
CPC .......... *A61M 5/002* (2013.01); *A61M 5/3205* (2013.01); *A61M 2005/3208* (2013.01)

(58) Field of Classification Search
CPC ................ A61M 5/002; A61M 5/3205; A61M 2005/3208; B65D 25/10; B65D 25/101; B65D 83/02

USPC .......................................... 206/366, 365, 438
See application file for complete search history.

(56) References Cited

U.S. PATENT DOCUMENTS

| | | | |
|---|---|---|---|
| 2002/0014430 A1 | 2/2002 | Groth | |
| 2002/0020647 A1* | 2/2002 | Groth | B65D 83/0454 |
| | | | 206/366 |
| 2007/0149924 A1* | 6/2007 | Marsh | A61M 5/002 |
| | | | 604/117 |
| 2010/0114035 A1 | 5/2010 | Schubert et al. | |
| 2011/0023281 A1 | 2/2011 | Schraga | |
| 2012/0037655 A1* | 2/2012 | DiBiasi | A61M 5/008 |
| | | | 53/449 |
| 2012/0041381 A1 | 2/2012 | Raj et al. | |
| 2014/0076758 A1* | 3/2014 | Dasbach | A61M 5/002 |
| | | | 206/366 |

(Continued)

FOREIGN PATENT DOCUMENTS

| CN | 1530144 A | 9/2004 |
|---|---|---|
| CN | 101443062 A | 5/2009 |

(Continued)

*Primary Examiner* — Steven A. Reynolds
(74) *Attorney, Agent, or Firm* — Greenberg Traurig, LLP; Roman Fayerberg; David J. Dykeman (57) ABSTRACT

A container (20) for storing pen needles (10) comprises a plurality of cavities (30), each cavity (30) having a closed end (32) and an open end (34), and a plurality of rings (40), each ring (40) including a plurality of arms (42) that is configured to retain the pen needle (10) in a first position and in a second position, wherein the open end (34) is flared outwardly, and the plurality of arms (42) are flared outwardly when the pen needle (10) is in the first position.

13 Claims, 12 Drawing Sheets

(56) References Cited

U.S. PATENT DOCUMENTS

2017/0233168 A1  8/2017  Horvath et al.

FOREIGN PATENT DOCUMENTS

| | | |
|---|---|---|
| CN | 104254355 A | 12/2014 |
| CN | 105451803 A | 3/2016 |
| CN | 206304176 U | 7/2017 |
| CN | 107405460 A | 11/2017 |
| CN | 210785700 U | 6/2020 |
| EP | 0903154 B1 | 9/1998 |
| JP | H11146912 A | 6/1999 |
| JP | 2004505683 A | 2/2004 |
| JP | 2007524471 A | 8/2007 |
| JP | 2014516661 A | 7/2014 |
| JP | 2016146947 A | 8/2016 |
| KR | 19990064388 A | 8/1999 |
| WO | 2013070789 A | 5/2013 |
| WO | 2017198589 A1 | 11/2017 |
| WO | WO2017189167 A1 | 11/2017 |
| WO | WO2017189172 A1 | 11/2017 |
| WO | WO2017189909 A1 | 11/2017 |
| WO | 2018050260 A1 | 3/2018 |
| WO | 2019210126 A1 | 10/2019 |

* cited by examiner

PEN NEEDLE STORAGE

CROSS-REFERENCE TO RELATED APPLICATION

This application claims priority under 35 U.S.C. 119(e) from U.S. provisional application Ser. No. 62/663,597, filed on Apr. 27, 2018, which is incorporated herein by reference in its entirety.

FIELD OF THE INVENTION

Various exemplary embodiments of the invention relate to medication pen needles.

BACKGROUND OF THE INVENTION

Medication pens are used to inject medication into a patient. A person who must periodically inject doses of medication will typically carry a medication pen and several pen needles. Each pen needle is designed for safety and sterility. However, inefficiencies and inconveniences arise. For example, storing a medication pen and several pen needles is typically achieved in a bulky housing. Typically, separate chambers in the housing hold new pen needles and used pen needles, which increases the volume required.

SUMMARY OF THE INVENTION

It is an aspect of the present invention to provide a pen needle storage container that provides an improved means of carrying multiple pen needles or cannulas. Such a container provides a single receptacle that has dual functionality of holding new and used pen needles. This allows for the dramatic reduction of the size (volume) of the device. These advantages are achieved via an interdigitated configuration that alternately places pen needle cavities in the container to maximize packing density. Also, after the pen needle is used, it is returned to its original location and locked into place to prevent future use. Accordingly, a separate disposal chamber is avoided. Further, the pen needle is positioned deeper within the container to reduce accessibility and minimize the risk of needle stick.

The foregoing and/or other aspects of the present invention can be achieved by providing a container for storing pen needles, the container comprising a plurality of cavities, each cavity having a closed end and an open end, and a plurality of rings, each ring including a plurality of arms that is configured to retain the pen needle in a first position and in a second position, wherein the open end is flared outwardly, and the plurality of arms are flared outwardly when the pen needle is in the first position.

The foregoing and/or other aspects of the present invention can also be achieved by providing a container for storing pen needles, the container comprising a plurality of cavities, each cavity comprising a closed end, an open end, and a plurality of protrusions that retains the pen needle in a first position and in a second position, and a plurality of rings that is each configured to engage a hub of the pen needle, wherein in the first position, one of the plurality of rings is disengaged from the hub of the pen needle, and in the second position, one of the plurality of rings is engaged to the hub of the pen needle.

The foregoing and/or other aspects of the present invention can further be achieved by providing a container for storing pen needles, the container comprising a plurality of cavities, each cavity comprising a closed end, an open end, a plurality of protrusions that retains the pen needle in a first position and in a second position, and a plurality of detents that is configured to engage a hub of the pen needle, wherein in the first position, the plurality of detents is disengaged from the hub of the pen needle, and in the second position, the plurality of detents is engaged to the hub of the pen needle.

The foregoing and/or other aspects of the present invention can additionally be achieved by providing a container for storing pen needles, the container comprising a plurality of cavities, each cavity having a closed end and an open end, wherein each of the cavities is configured to receive a pen needle in a plurality of positions to indicate status.

The foregoing and/or other aspects of the present invention can also be achieved by providing a method of using a plurality of pen needles stored in container, the method comprising connecting a unused pen needle to a medication delivery pen for medication delivery; removing the unused pen needle from a first position in a cavity of the container; administering medication via the pen needle connected to the medication delivery pen; disposing of the used pen needle, after medication delivery, in a second position in the cavity of the container; and sending the container to a manufacturer or a waste management entity after use of all of the plurality of pen needles in the container.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
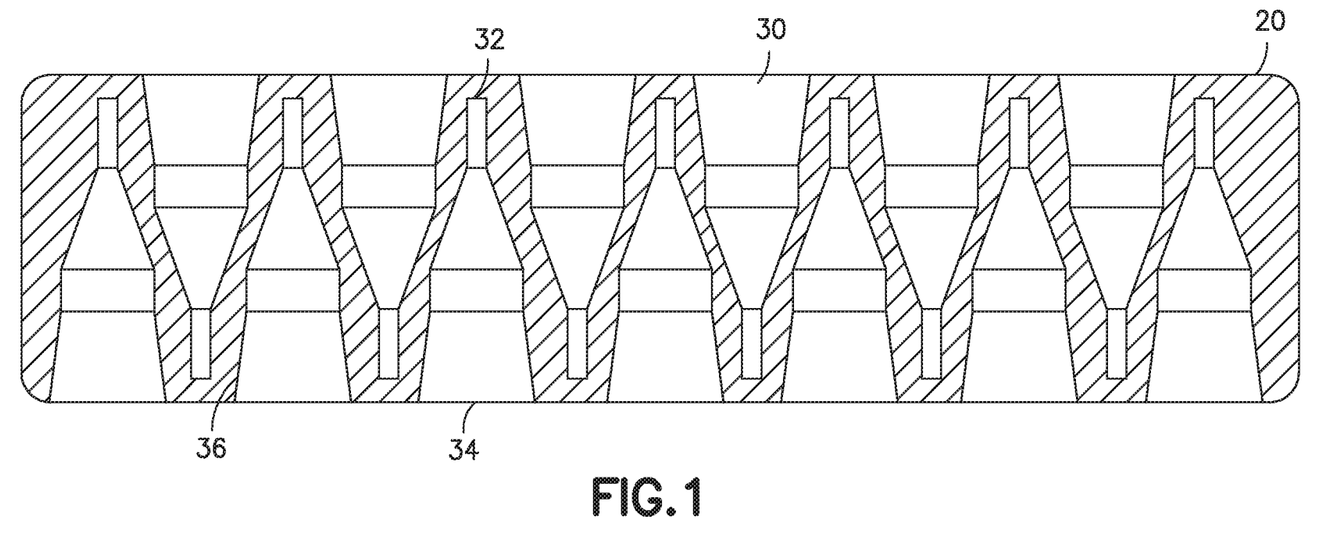
FIG. 1 illustrates a top cross-sectional view of an exemplary pen needle storage container.

FIG. 1 illustrates a cross-sectional view of a pen needle storage container 20 having a plurality of cavities 30. The cavities 30 each have an open end 34 configured to receive a grip ring 40 and a pen needle 10 (illustrated in subsequent figures), and a closed end 32. Each of the cavities 30 is configured to receive the pen needle 10 in a plurality of positions to indicate status. Each of the open ends 34 include a flared opening 36 to allow for expansion and contraction of the grip ring 40 as described below.

The plurality of cavities 30 are advantageously arranged in an interdigitated manner, as shown, to provide alternate cavity placement. This configuration optimizes space by dramatically reducing the required volume of the device and maximizes the packing density. Also, multiple pen needles 10 can be carried in the pen needle storage container 20, thus making it convenient to carry.

Figure 2:
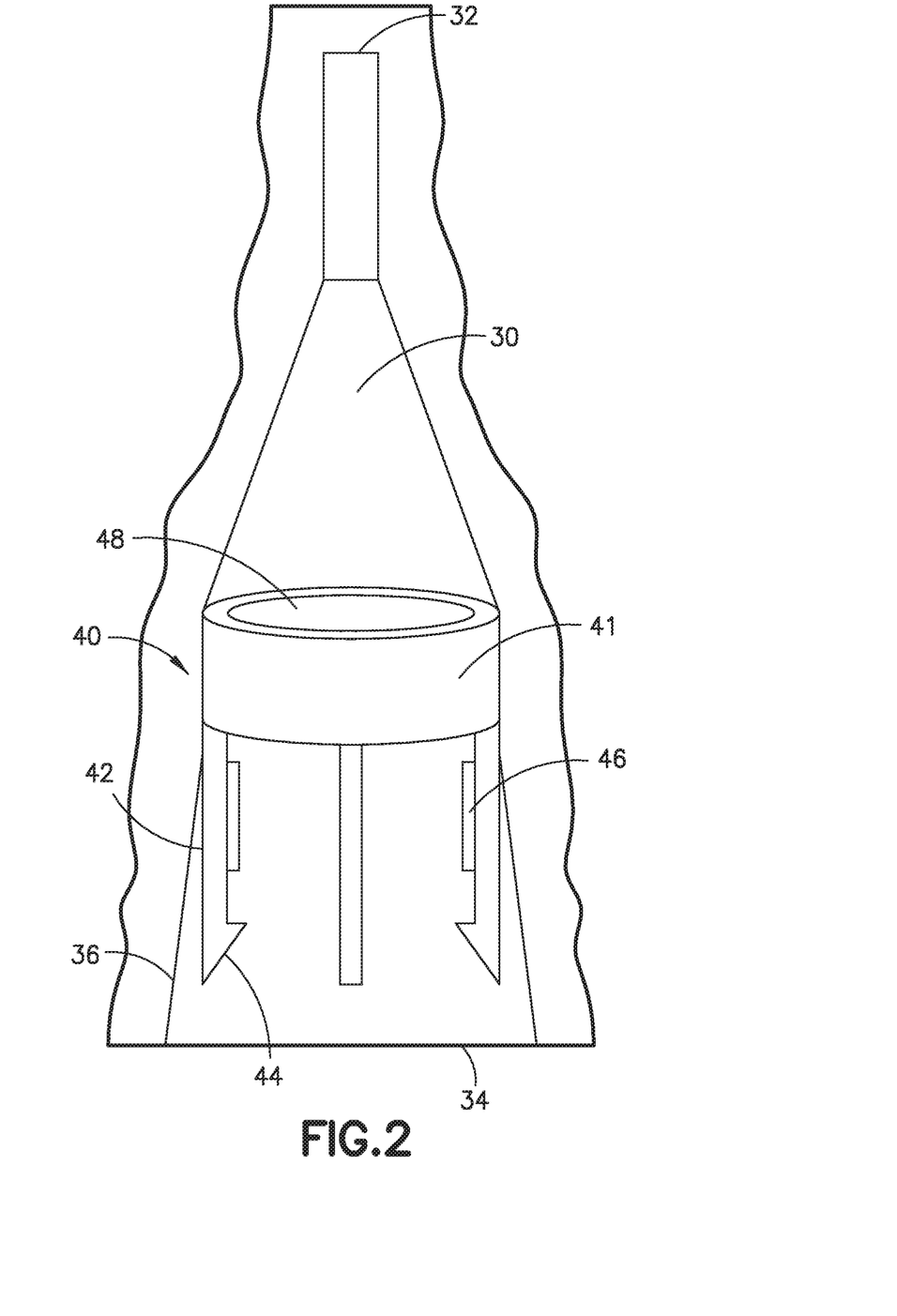
FIG. 2 illustrates a transparent top perspective view of a cavity in the pen needle storage container of FIG. 1.

FIG. 2 illustrates the grip ring 40 in one of the plurality of cavities 30 of the pen needle storage container 20. The grip ring 40 is made of metal or plastic, for example, and is axially and rotationally fixed to an inner wall of one of the cavities 30 via glue, for example. Although not described, other means of securing the grip ring 40 to the cavity 30 of the pen needle storage container 20 commonly understood by one skilled in the art are contemplated herein. The grip ring 40 is preferably a separate component and not integral to the cavity 30 of the pen needle storage container 20 because of difficulties in molding and manufacturing.

The grip ring 40 includes a plurality of arms 42 extending from a base 41 of the grip ring 40. In its free and unbiased state, the plurality of arms 42 are substantially perpendicular to a surface of the base 41. Each arm 42 includes a tapered jaw 44 disposed at an end opposite to the base 41. The arms 42 and the tapered jaw 44 are used to capture and secure the pen needle 10. The grip ring 40 also includes a plurality of protrusion 46 to further secure the pen needle 10. Finally, an opening 48 extends through the base 41 of the grip ring 40 to provide a space for a needle in the pen needle 10 to extend into.

Figure 3:
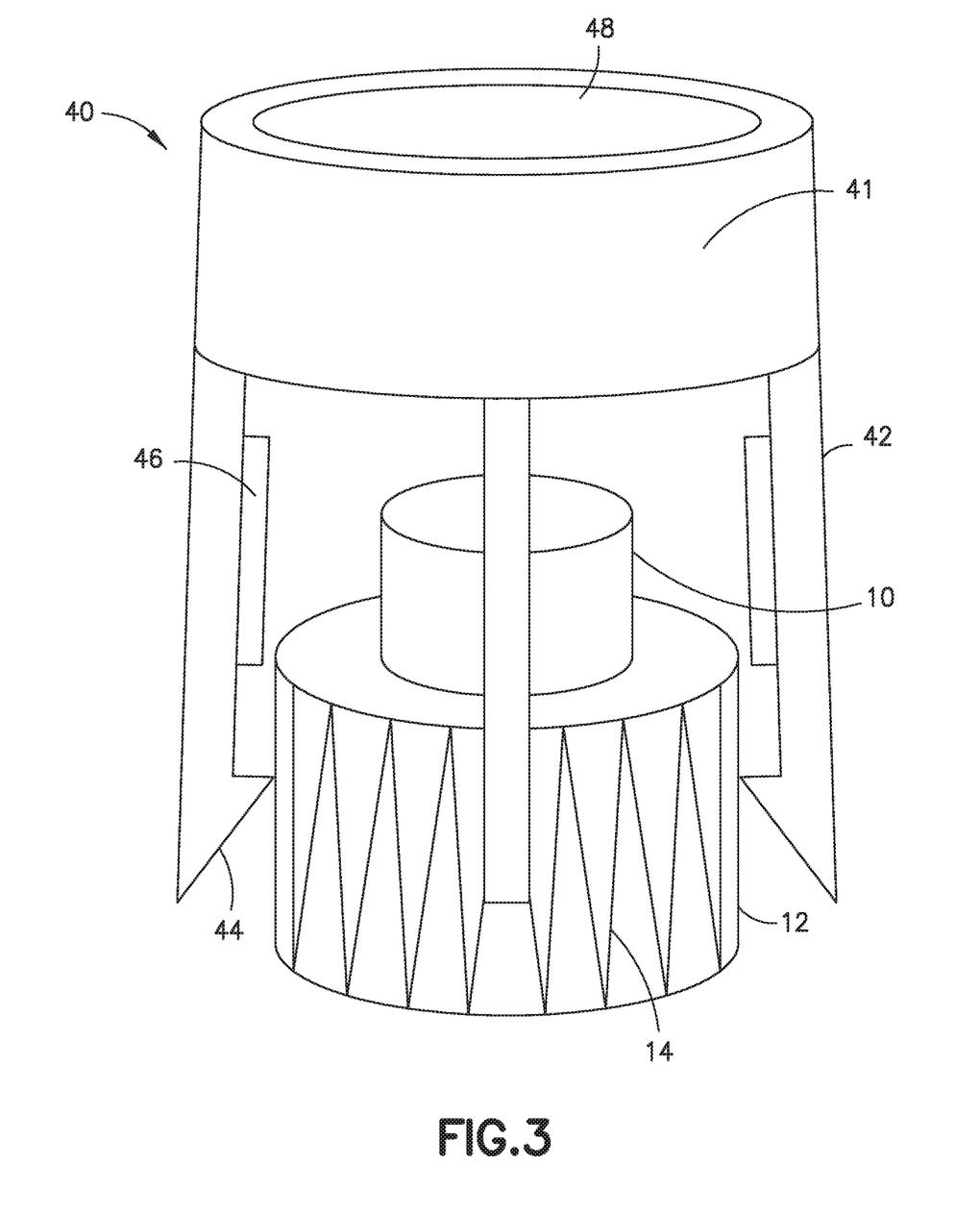
FIG. 3 illustrates a top perspective view of a grip ring holding a pen needle of FIG. 2 in a first position.

A first position between the grip ring 40 and the pen needle 10 is illustrated in FIG. 3. In this position, the pen needle 10 has yet to be used and is ready for future use. The pen needle 10 includes a hub 12 having castellations 14, such as notches, that engage the tapered jaws 44 of the grip ring 40. The engagement between the castellations 14 and the tapered jaws 44 provide rotational resistance to the pen needle 10.

Such engagement allows for a medication delivery pen to engage and be secured to the pen needle 10 via rotation of the medication delivery pen. Specifically, a non-patient end of the pen needle 10 punctures the pen cartridge septum (not shown) to provide fluid engagement to the medication delivery pen. Although the pen needle 10 is not rotationally or axially fixed in the first position, significant resistance is provided so that the pen needle 10 is secured and not rotating when the medication delivery pen is secured to the pen needle 10.

When the grip ring 40 is engaged to the pen needle 10 in the first position, the arms 42 of the grip ring 40 are flared outwardly via elastic deformation. This is a biased position of the grip ring 40 and provides additional holding strength between the grip ring 40 and the pen needle 10. Finally, the opening at the base 41 of the grip ring 40 provides a space for the needle of the pen needle 10 to extend into.

Figure 4:
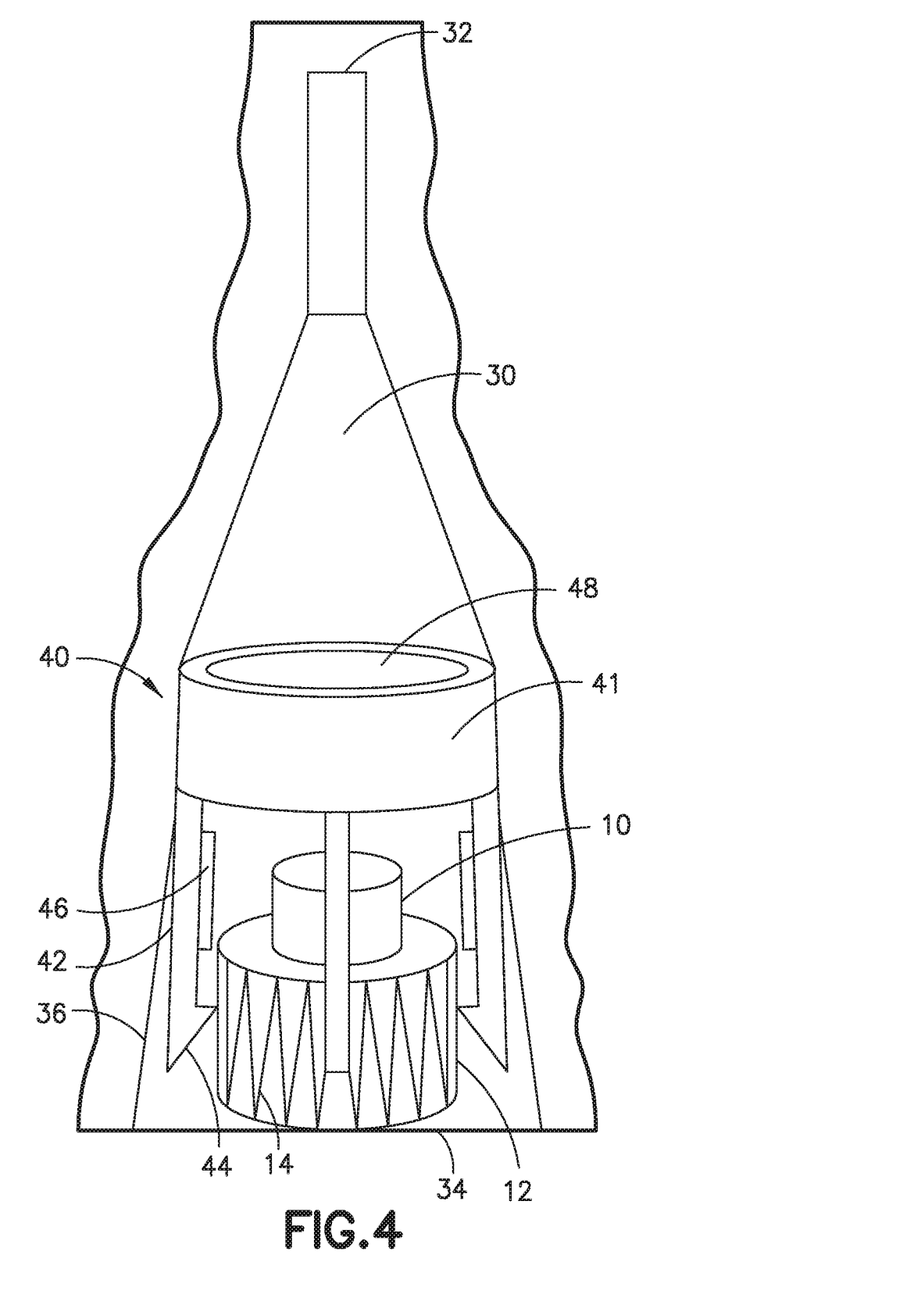
FIG. 4 illustrates a transparent top perspective view of the grip ring holding the pen needle of FIG. 3 in the cavity of the pen needle storage container.

FIG. 4 illustrates the grip ring 40 and the pen needle 10 of FIG. 3 in one of the plurality of cavities 30 of the pen needle storage container 20. The outwardly flared arms 42 of the grip ring 40 are accommodated in the flared openings 36 at the open end 34 of the cavities 30. Also, in the first position, a proximal end of the pen needle 10 is disposed near the open end 34 of the cavity 30 for easier accessibility by a user to affix the pen needle 10 to the medication delivery pen.

Specifically, when the pen needle 10 is in the first position, the medication delivery pen can engage the pen needle 10 and rotate to secure the pen needle 10 to the medication delivery pen. Subsequently, the user pulls the medication delivery pen from the pen needle storage container 20 to remove the new pen needle 10. The medication delivery pen is now ready to administer medication via the pen needle 10. Accordingly, when the pen needle 10 is in the first position, the status of the pen needle 10 is unused, retrievable and/or in a shallow position within the cavity 30 of the pen needle storage container 20.

Figure 5:
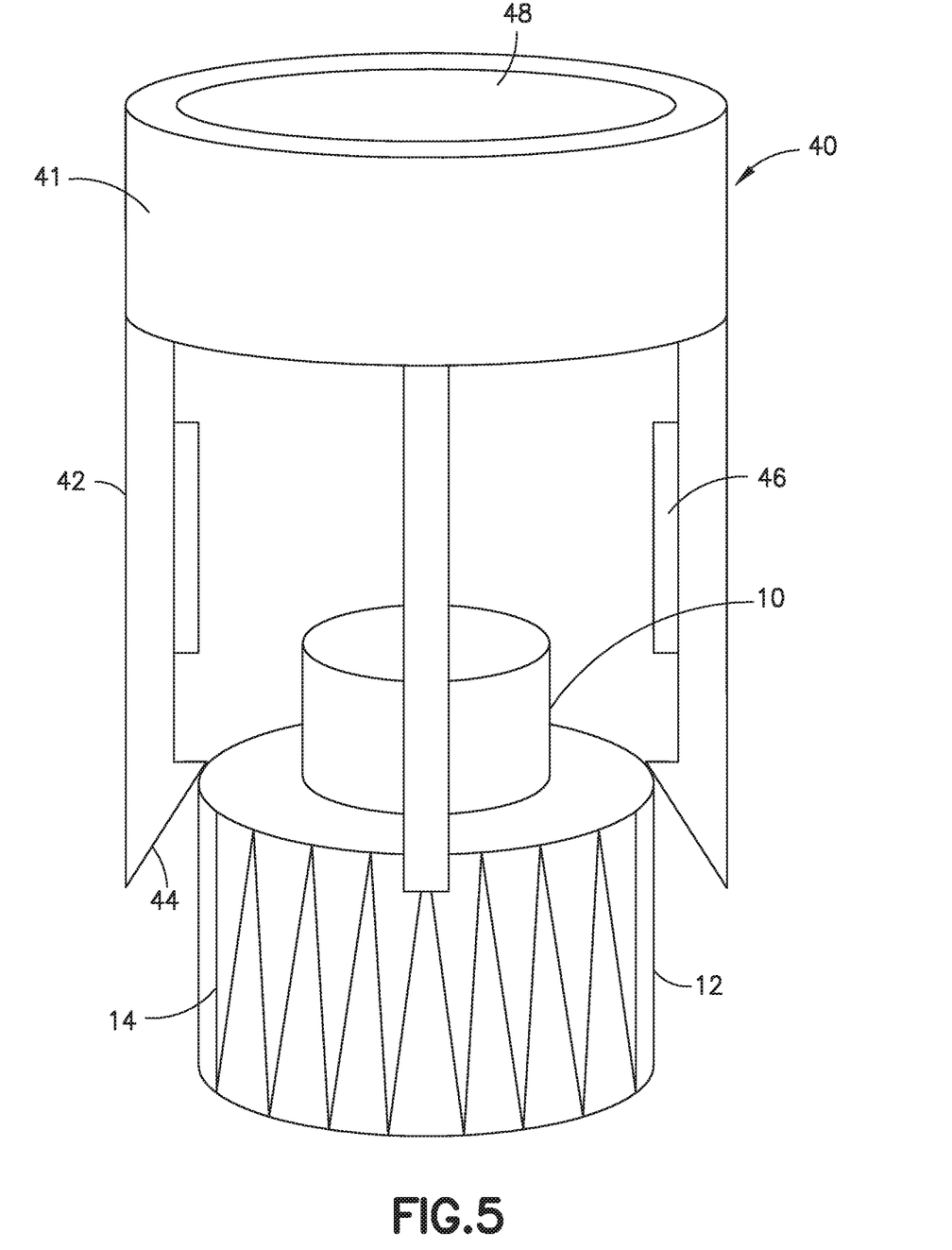
FIG. 5 illustrates an alternate embodiment of a top perspective view of a grip ring holding a pen needle of FIG. 2 in the first position.

In an alternate embodiment, FIG. 5 also illustrates the grip ring 40 and the pen needle 10 in the first position where the tapered jaws 44 engage the hub 12 of the pen needle 10 but do not fully engage the castellations 14. In this embodiment, portions of the tapered jaws 44 are disposed distal to a distal end of the hub 12 of the pen needle 10. Further, the arms 42 are not outwardly flared, thus not providing an additional gripping force to the hub 12 of the pen needle 10. That is, in the first position of this embodiment, the grip ring 40 is in its natural, unbiased state. Such a configuration reduces and optimizes the overall space of the cavity 30 in the pen needle storage container 20.

In this configuration, similar benefits as described above are achieved. Specifically, the engagement between the tapered jaws 44 and the hub 12 provides rotational resistance to the hub 12. Also, the proximal end of the pen needle 10 is even further positioned near to the open end 34 of the cavity 30 for easier accessibility by the user to affix the pen needle 10 to the medication delivery pen.

Figure 6:
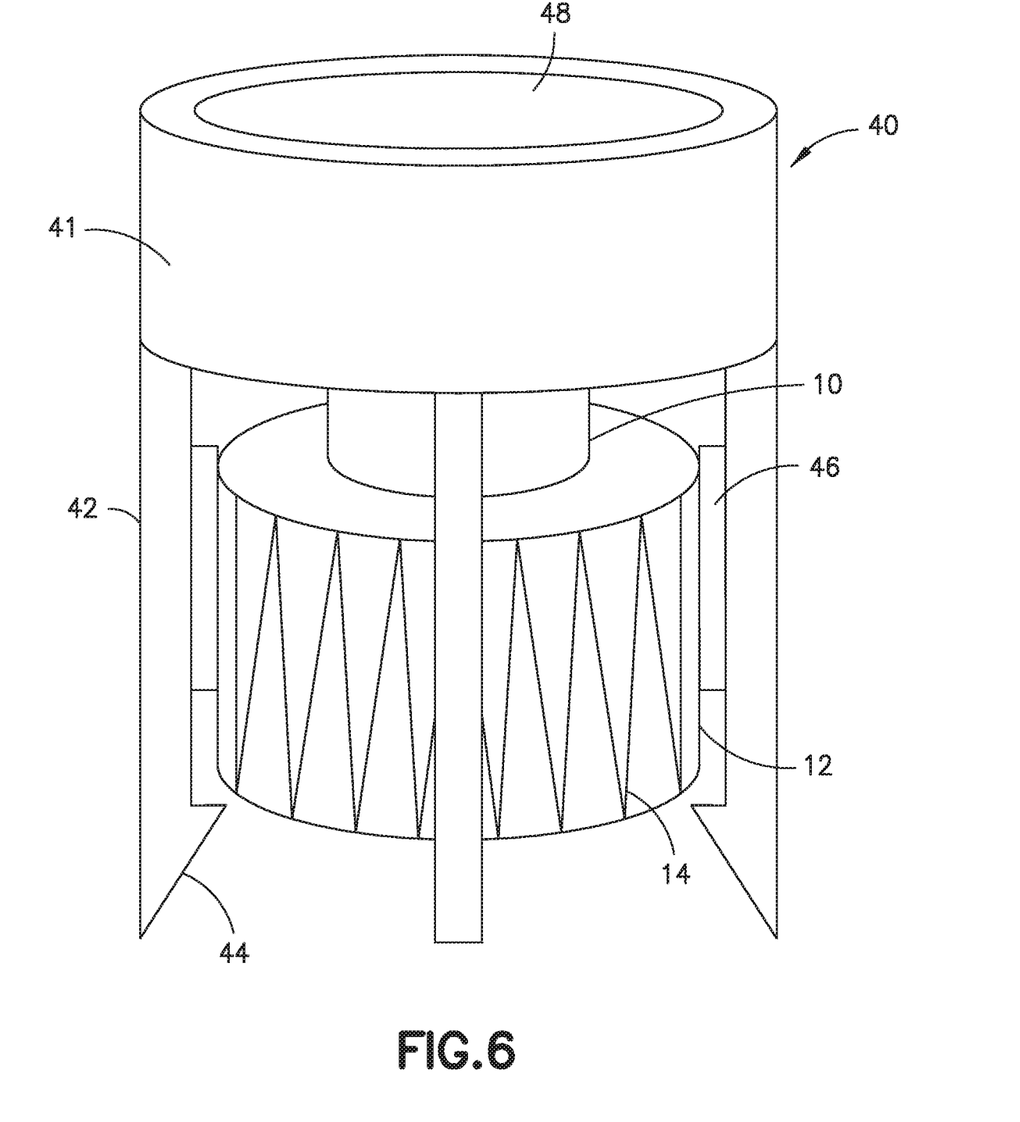
FIG. 6 illustrates a top perspective view of the grip ring holding the pen needle of FIG. 3 in a second position.

FIG. 6 illustrates the pen needle 10 enclosed in the grip ring 40 in a second position. The second position locks and secures the pen needle 10 in the grip ring 40 and prevents future use of the pen needle 10. Specifically, after the pen needle 10 is used, the user places the pen needle 10 into the grip ring 40 while the pen needle 10 is connected to the medication delivery pen. The tapered jaws 44 initially flare outwardly in a biased position to receive the pen needle 10.

When the pen needle 10 finally reaches the second position, the proximal end of the tapered jaws 44 extend beyond the proximal end of the pen needle 10. The user then rotates the medication delivery pen and disengages it from the used pen needle 10. In this position, the arms 42 and the tapered jaws 44 do not substantially flare outward. Instead, the arms 42 and the tapered jaws 44 elastically return to its original, free state and partially enclose and lock the pen needle 10 to the grip ring 40.

Also, in the second position, an outer diameter of the hub 12 of the pen needle 10 is greater than the inner diameter of the tapered jaws 44 of the grip ring 40. In this manner, the grip ring 40 provides a physical barrier to prevent the pen needle 10 from being removed for further use.

The pen needle 10 is also disposed deeper within the grip ring 40 of the pen needle storage container 20. Such a configuration advantageously makes the used pen needle 10 less accessible. This is beneficial because a used pen needle 10 should not be reused. The lower positioning of the used pen needle 10 in the second position also minimizes the risk of needle sticks and improves safety.

The pen needle 10 is further locked into place in the second position via the protrusions 46. A protrusion 46 extend along an inner surface of each of the plurality of arms 42 of the grip ring 40. The protrusions 46 contact the castellations 14 of the hub 12 of the pen needle 10 and apply a compression force to secure the pen needle 10. Accordingly, the pen needle 10 is locked rotationally and axially in the grip ring 40. The additional force provides further resistance and secures the pen needle 10 within the grip ring 40 in the second position. Also, the additional force advantageously allows the pen needle 10 to be more easily removed from the medication delivery pen.

Figure 7:
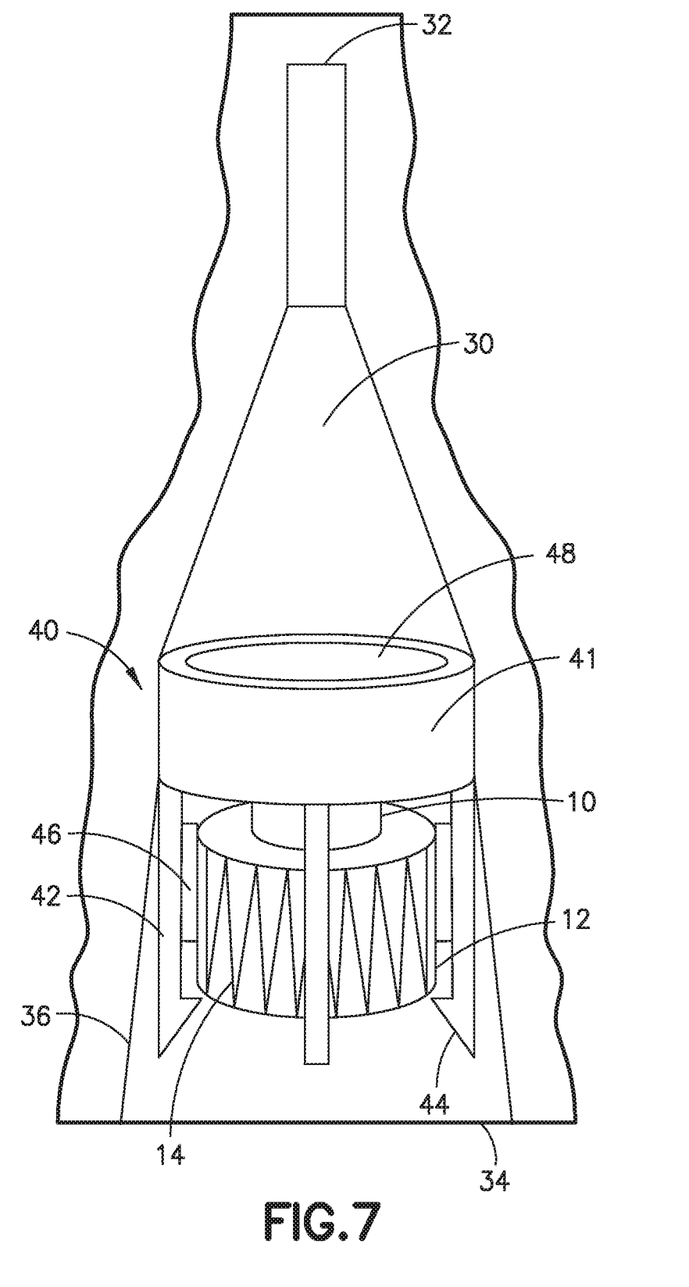
FIG. 7 illustrates a transparent top perspective view of the grip ring holding the pen needle of FIG. 6 in the cavity of the pen needle storage container.

FIG. 7 illustrates the pen needle 10 enclosed in the grip ring 40 in the second position of FIG. 6 while being disposed in one of the plurality of cavities 30 of the pen needle storage container 20. The second position of the pen needle 10 is disposed deeper within the open end 34 of the pen needle storage container 20 than the first position. The flared opening 36 at the open end 34 of the cavity 30 allow for the arms 42 of the grip ring 40 to flare outwardly when initially engaged to the pen needle 10 and subsequently contract to its free position when the pen needle 10 is locked in the grip ring 40 in the second position. Accordingly, when the pen needle 10 is in the second position, the status of the pen needle 10 is used, irretrievable and/or in a deeper position within the cavity 30 of the pen needle storage container 20.

Figure 8:
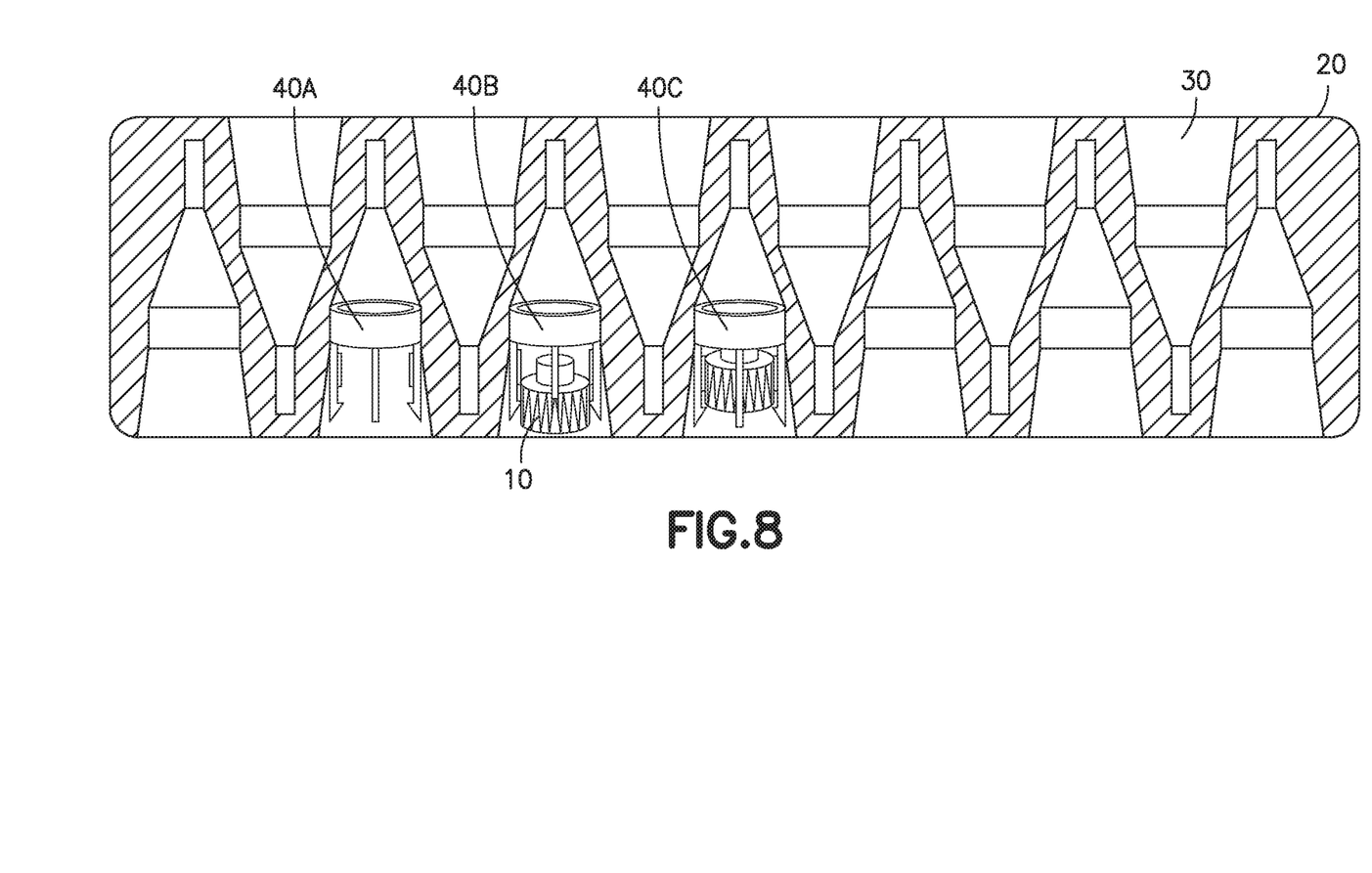
FIG. 8 illustrates a top cross-sectional view of an exemplary pen needle storage container with three different conditions of the grip ring and the pen needle of FIG. 2.

FIG. 8 illustrates a cross sectional view of the pen needle storage container 20 with the grip ring 40A, 40B, 40C in a plurality of configurations stored in the plurality of cavities 30. Specifically, grip ring 40A is disposed in one of the cavities 30 without a pen needle 10. Grip ring 40B is disposed in one of the cavities 30 with a pen needle 10 in the first position as illustrated in FIG. 4. Grip ring 40C is disposed in one of the cavities 30 with a pen needle 10 in the second position as illustrated in FIG. 7.

As illustrated in FIG. 8, the cavities 30 are advantageously used for multiple configurations of the grip rings 40 and the pen needles 10. Specifically, one cavity 30 is advantageously used for a new pen needle 10 in the first position and later used for a used pen needle 10 in the second position. Such a configuration provides, at least, temporary containment for the used pen needles 10 (contaminated sharps) to be placed in the pen needle storage container 20 after use.

Finally, after all the pen needles 10 are used and returned to the second position in each of the cavities 30 of the pen needle storage container 20, the user can advantageously send the pen needle storage container 20, via mail, for example, to a manufacturer or a waste management entity for safe and sterile disposal. Optionally, the manufacturer can advantageously recycle and reuse various components of the pen needle storage container 20. For example, the manufacturer can sterilize and reuse some or all of the cavities 30 in the pen needle storage container 20. Specifically, the manufacturer can replace the used pen needle 40 with the unused pen needle 10 in one or more of the cavities 30. The pen needle storage container 20 can then be shipped and ultimately sold for reuse.

Figure 9:
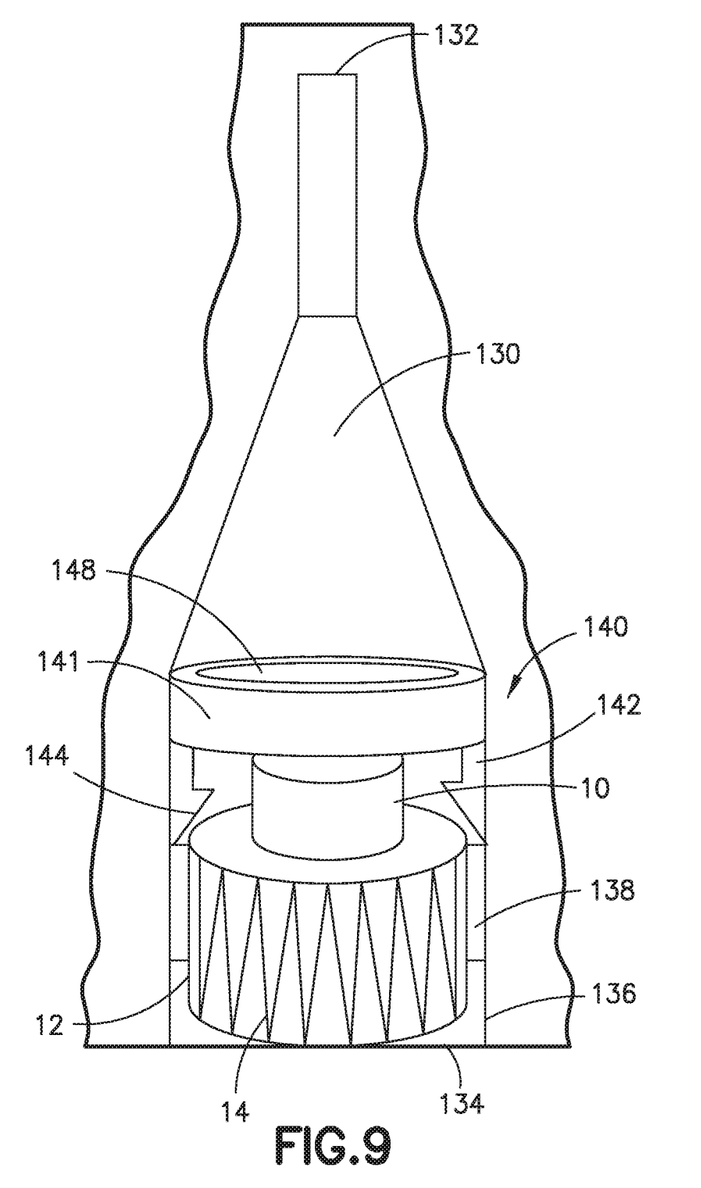
FIG. 9 illustrates a transparent top perspective view of a second exemplary embodiment of a grip ring and a pen needle in a first position in a cavity of a pen needle storage container.
Figure 10:
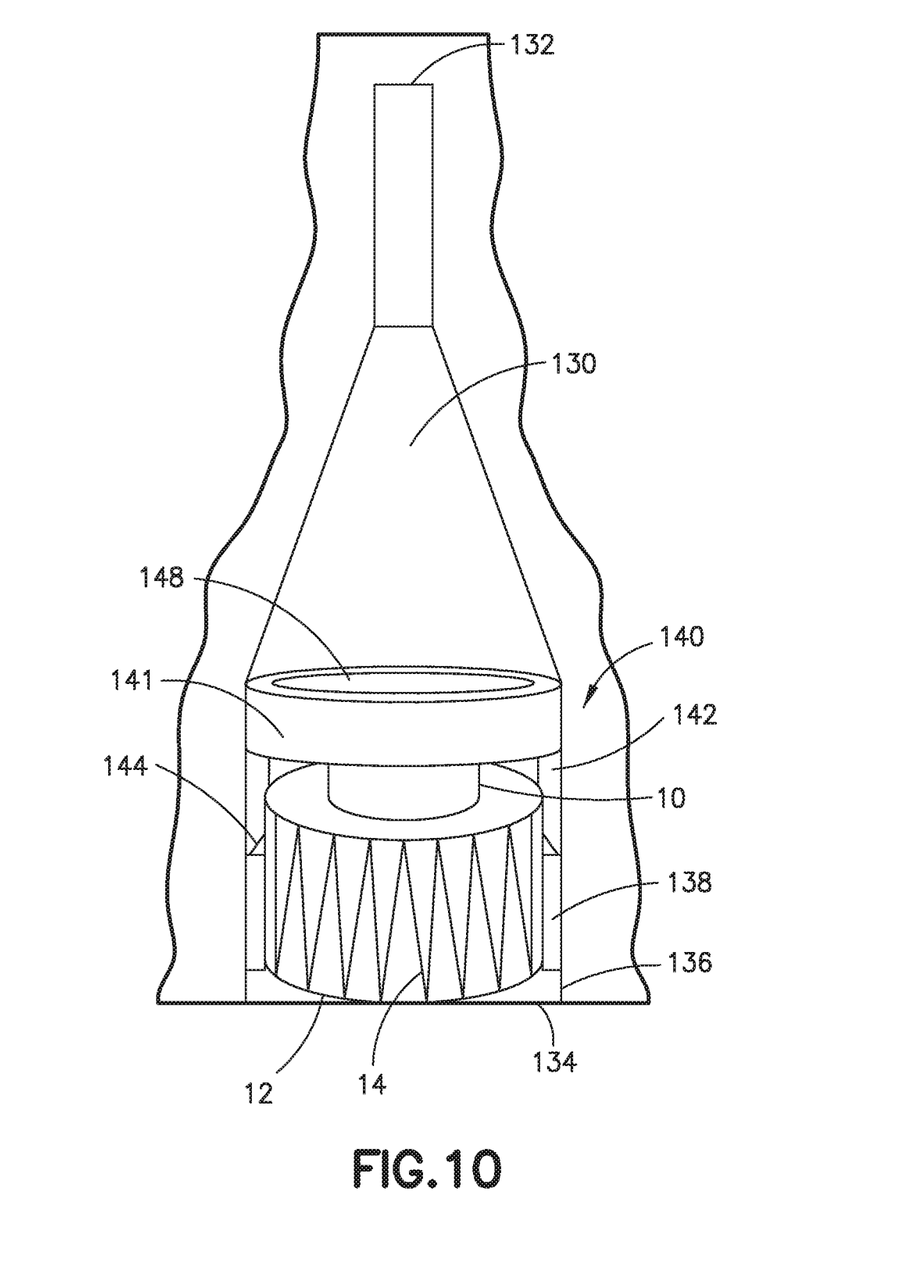
FIG. 10 illustrates a transparent top perspective view of the grip ring and the pen needle of FIG. 9 in a second position in the cavity of the pen needle storage container.

FIGS. 9 and 10 illustrate a second exemplary embodiment of a cavity 130 of a pen needle storage container. This embodiment is similar to the embodiment described above with the following differences. In this embodiment, the pen needle storage container includes the plurality of cavities 130 each having a closed end 132 and an open end 134. However, at the open end 134 of each of the cavities 130, a straight wall opening 136 is present. Such a configuration advantageously takes less space within the pen needle storage container.

Further, a plurality of protrusions 138 are disposed near the proximal end of the open end 134 of the cavities 130. The protrusions 138 are preferably molded into an inner wall of the cavity 130 as a rib, although other manufacturing and design configurations are contemplated herein. Each of the cavities 130 of the pen needle storage container also includes a grip ring 140 having a base 141, a plurality of arms 142, a plurality of tapered jaws 144 and an opening 148 as similarly described above.

In a first position, as illustrated in FIG. 9, the pen needle 10 is retained in the cavity 130 via the plurality of protrusions 138. Each protrusion 138 engages the castellations 14 in the pen needle 10 and provide rotational resistance while securing the pen needle 10 in the cavity 130. Although the pen needle 10 is not rotationally or axially fixed in the first position, significant resistance is provided so that the pen needle 10 is secured and not rotating when the medication delivery pen is secured to the pen needle 10.

The grip ring 140 is also disengaged from the pen needle 10 in the first position. However, the needle of the pen needle 10 may extend through the opening 148 in the base 141 of the grip ring 140. The pen needle 10 is also disposed near the open end 134 of the cavity 130 for easy accessibility.

In a second position, as illustrated in FIG. 10, the protrusions 138 of the cavity 130, in addition to the tapered jaws 144 of the grip ring 140 engage the castellations 14 in the pen needle 10 and provide rotational resistance while securing the pen needle 10 in the cavity 130. In this position, the pen needle 10 is rotationally and axially locked inside the cavity 130 and cannot be removed for further use.

Also, the pen needle 10 is disposed deeper in the cavity 130 and farther away from the open end 134 than compared to the first position illustrated in FIG. 9. This is beneficial because a used pen needle 10 should not be reused. Such a configuration advantageously makes the used pen needle 10 less accessible. The lower positioning of the used pen needle 10 in the second position also minimizes the risk of needle sticks and improves safety.

Figure 11:
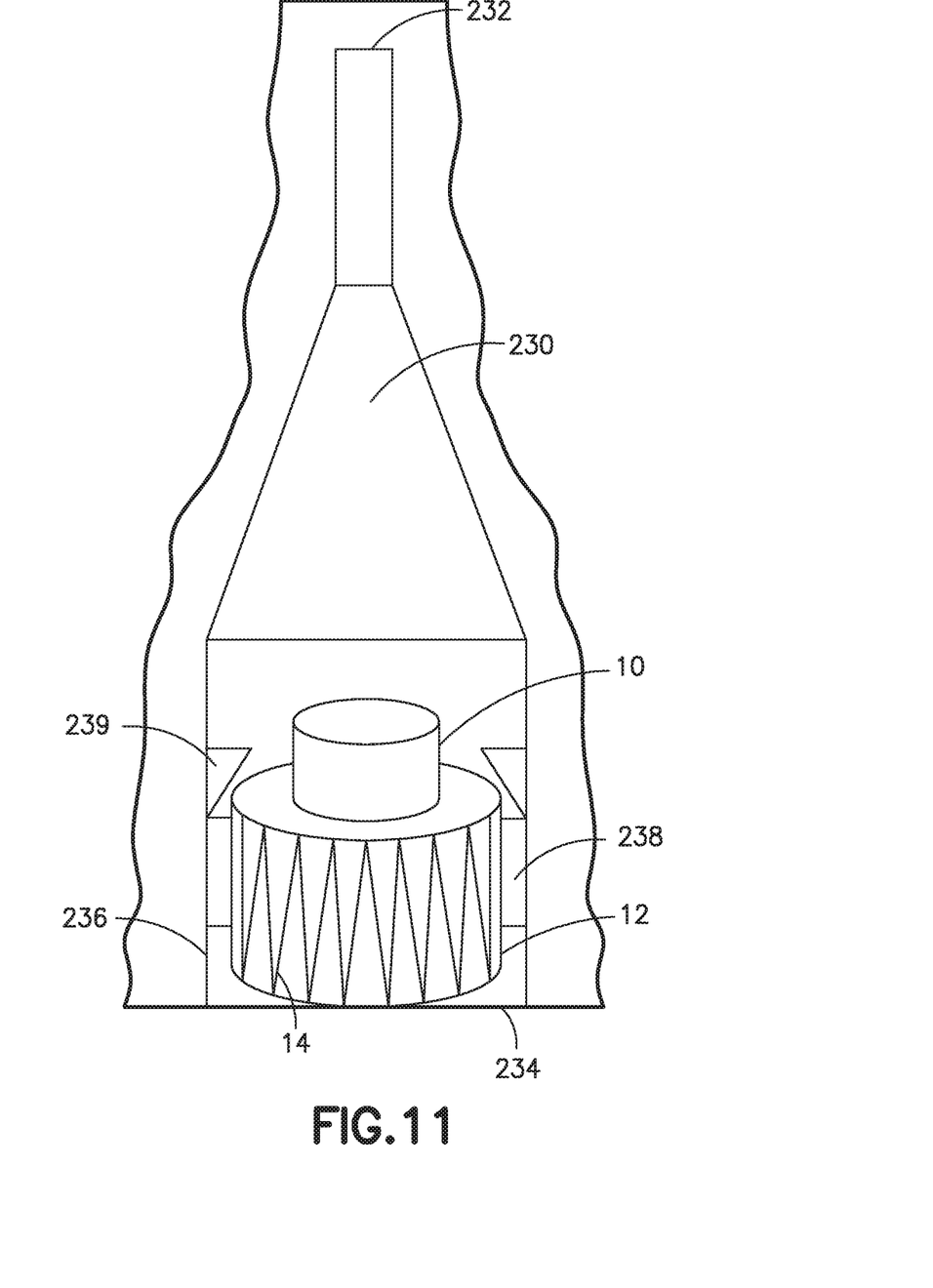
FIG. 11 illustrates a transparent top perspective view of a third exemplary embodiment of a cavity of a pen needle storage container with a pen needle in a first position.
Figure 12:
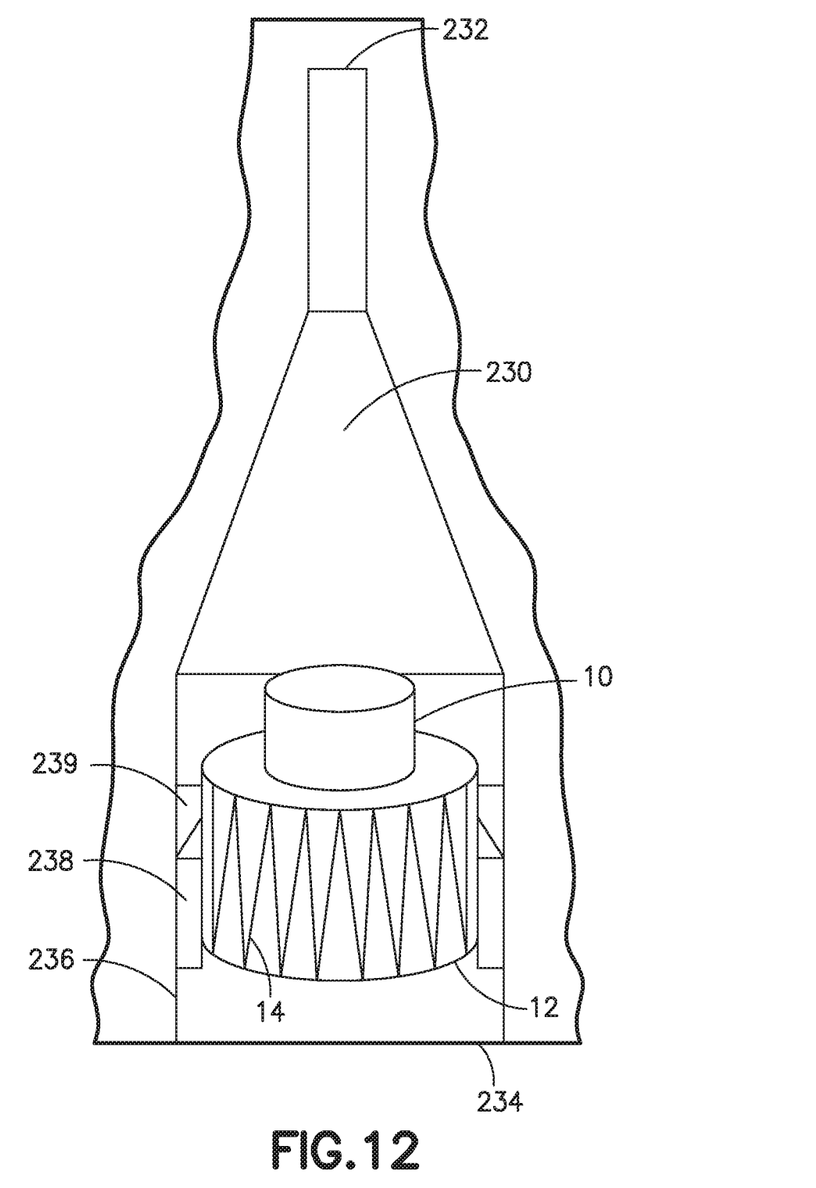
FIG. 12 illustrates a transparent top perspective view of the cavity of the pen needle storage container with the pen needle of FIG. 11 in a second position.

FIGS. 11 and 12 illustrate a third exemplary embodiment of a plurality of cavities 230 in a pen needle storage container. This embodiment is similar to the embodiment described above with the following differences. In this embodiment, the pen needle storage container includes the plurality of cavities 230 each having a closed end 232 and an open end 234 with a straight wall opening 236. The cavity 230 further includes a plurality of protrusions 238 and a plurality of detents 239. The protrusions 238 and detents 239 are molded within the cavity 230, although other manufacturing and design configurations are contemplated herein. The cavity 230 does not include a grip ring.

In a first position, as illustrated in FIG. 11, the pen needle 10 is retained in the cavity 230 via the protrusions 238. The protrusions 238 engage the castellations 14 in the pen needle 10 and provide rotational resistance while securing the pen needle 10 in the cavity 230. However, the pen needle 10 is not in contact with the plurality of detents 239. Although the pen needle 10 is not rotationally or axially fixed in the first position, significant resistance is provided so that the pen needle 10 is secured and not rotating when the medication delivery pen is secured to the pen needle 10. The pen needle 10 is also disposed near the open end 134 of the cavity 130 for ease of accessibility.

In a second position, as illustrated in FIG. 12, the protrusions 238 of the cavity 230, in addition to the detents 239 engage the castellations 14 in the pen needle 10 and provide rotational resistance and interference while securing the pen needle 10 in the cavity 230. Preferably, in this position, the detents 239 deform to lock the pen needle 10 in the cavity 230 and prevent removal for further use.

In another embodiment, the detents 239 do not deform. Rather, the detents 239 are composed of a hard plastic or a metallic material such as a metallic spike. When the pen needle 10 engages the detents 239, the pen needle 10 plastically deforms in a manner similar to a fish hook engagement or a barbed interface. Accordingly, the pen needle 10 is rotationally and axially locked, as well as not reusable.

Also, the pen needle 10 is disposed deeper in the cavity 230 and farther away from the open end 234. This is beneficial because a used pen needle 10 should not be reused. Such a configuration advantageously makes the used pen needle 10 less accessible. The lower positioning of the used pen needle 10 in the second position also minimizes the risk of needle sticks and improves safety.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A container for storing pen needles, the container comprising:
   a plurality of cavities, each cavity having a closed end and an open end; and
   a plurality of rings, each ring including a plurality of arms that is configured to retain a pen needle in a first position and in a second position;
   wherein the open end is flared outwardly; and
   the plurality of arms are configured to flare outwardly when the pen needle is in the first position and the plurality of arms are configured to come together to lock the pen needle in place in the second position;
   wherein a plurality of protrusions extends inward from the plurality of arms.

2. The container of claim 1, wherein the plurality of cavities are interdigitated.

3. A container for storing pen needles, the container comprising:
   a plurality of cavities, each cavity having a closed end and an open end; and
   a plurality of rings, each ring including a plurality of arms that is configured to retain a pen needle in a first position and in a second position; wherein
   the open end is flared outwardly; and
   the plurality of arms are flared outwardly when the pen needle is in the first position;
   wherein a plurality of protrusions extends inward from the plurality of arms
   wherein the plurality of arms of each of the plurality of rings each includes a tapered jaw to form a plurality of tapered jaws; the pen needle includes a hub; and in the first position, the plurality of tapered jaws of one of the plurality of rings engage the hub of the pen needle.

4. The container of claim 3, wherein a portion of the plurality of tapered jaws is disposed below a distal end of the hub of the pen needle.

5. The container of claim 3, wherein the hub of the pen needle includes castellations that engage the plurality of tapered jaws.

6. The container of claim 3, wherein the hub of the pen needle does not substantially rotate when engaged to the plurality of tapered jaws in the first position.

7. A container for storing pen needles, the container comprising:
   a plurality of cavities, each cavity having a closed end and an open end; and
   a plurality of rings, each ring including a plurality of arms that is configured to retain a pen needle in a first position and in a second position; wherein
   the open end is flared outwardly; and
   the plurality of arms are flared outwardly when the pen needle is in the first position;
   wherein a plurality of protrusions extends inward from the plurality of arms
   wherein
   the plurality of arms of each of the plurality of rings each includes a tapered jaw to form a plurality of tapered jaws;
   the pen needle includes a hub; and
   in the second position, the plurality of arms and the plurality of tapered jaws of one of the plurality of rings at least partially enclose the hub of the pen needle.

8. The container of claim 7, wherein the plurality of tapered jaws are disposed beyond a proximal end of the hub of the pen needle.

9. The container of claim 7, wherein the plurality of protrusions are configured to engage the hub of the pen needle to secure the pen needle to one of the plurality of rings.

10. The container of claim 1, wherein the pen needle is locked in one of the plurality of rings in the second position and unable to be removed.

11. The container of claim 1, wherein the pen needle in the second position is disposed at a position deeper inside the container than the pen needle in the first position.

12. The container of claim 1, wherein
    each of the plurality of rings includes a base having an opening; and a needle of the pen needle extends through the opening in the first position and the second position.

13. A container for storing pen needles, the container comprising:
a plurality of cavities, each cavity comprising:
a closed end;
an open end; and
a plurality of protrusions that retains a pen needle in a first position and in a second position; and
a plurality of rings each including a plurality of arms configured to engage a hub of the pen needle;
wherein
in the first position, one of the plurality of rings is disengaged from the hub of the pen needle; and
in the second position, one of the plurality of rings is engaged to the hub of the pen needle;
wherein the plurality of protrusions extends inward from the plurality of arms
wherein the hub includes castellations that engage a plurality of tapered jaws of the plurality of rings in the second position.

* * * * *